United States Patent [19]
Blaschke et al.

[11] Patent Number: 5,281,722
[45] Date of Patent: Jan. 25, 1994

[54] PREPARATION AND USE OF SALTS OF THE PURE ENANTIOMERS OF ALPHA-LIPOIC ACID

[75] Inventors: Gottfried Blaschke, Münster; Ursula Scheidemantel, Münster/Hiltrup; Horst Bethge, Hanau-Wolfgang; Roland Möller, Hammersbach; Thomas Beisswenger, Bad Vilbel; Klaus Huthmacher, Gelnhausen, all of Fed. Rep. of Germany

[73] Assignee: Degussa AG, Fed. Rep. of Germany

[21] Appl. No.: 975,075

[22] Filed: Nov. 12, 1992

[30] Foreign Application Priority Data

Nov. 16, 1991 [DE] Fed. Rep. of Germany ....... 4137773

[51] Int. Cl.$^5$ ............... C07D 339/04; C11C 3/00
[52] U.S. Cl. ..................... 549/39; 554/102; 562/401; 564/304
[58] Field of Search .............. 562/401, 512, 606; 549/39; 514/440; 564/304; 554/102

[56] References Cited

U.S. PATENT DOCUMENTS 4,772,727  9/1988  Sutherland et al. ............... 549/39
4,973,745  11/1990  Blasche et al. ..................... 562/401

OTHER PUBLICATIONS

*Journal of the American Chemical Society;* V. 79, Nr. 24; Dec. 20, 1957, pp. 6483–6487.
*Chemical Abstracts;* vol. 94, No. 13, Mar. 30, 1981; Abstract No. 103722g.
*Chemical Abstracts;* vol. 63, No. 13; Dec. 20, 1965; Abstract No. 17809b.

*Primary Examiner*—Paul F. Shaver
*Assistant Examiner*—Vera C. Clarke
*Attorney, Agent, or Firm*—Cushman, Darby & Cushman

[57] ABSTRACT

The pure enantiomers of alpha-lipoic acid are obtained by formation of the diastereomeric salt pairs with the optical antipodes of alpha-methylbenzylamine in solution.

10 Claims, No Drawings

PREPARATION AND USE OF SALTS OF THE PURE ENANTIOMERS OF ALPHA-LIPOIC ACID

The present invention relates to new optically active salts of alpha-lipoic acid and of optically active alpha-methylbenzylamine. The invention also relates to a process for the preparation of enantiomerically pure alpha-lipoic acids and enantiomerically pure dihydrolipoic acids.

BACKGROUND OF THE INVENTION

Alpha-lipoic acid is 1,2-dithiolane-3-pentanoic acid (thioctic acid).

As a coenzyme of alpha-ketonic acid dehydrogenases, alpha-lipoic acid is widespread in plants and animals; the naturally occurring form has the R-configuration. However, when "alpha-lipoic acid" is referred to below, it is always an alpha-lipoic acid of unknown stereochemical composition.

Alpha-lipoic acid is pharmacologically active and has anti-inflammatory and antinociceptive (analgesic) as well as cytoprotective properties.

A series of salts of alpha-lipoic acid are known, for example salts of alpha-lipoic acid with optically active bases such as salts with the basic amino acids arginine and lysine. (See Spanish patent No. 313,056). Neither the reaction of L-arginine with D,L-alpha-lipoic acid nor the reaction of DL-lysine with D,L-alpha-lipoic acid yields separable diastereomeric salt pairs.

Known syntheses of enantiomerically pure alpha-lipoic acid always include chiral primary steps which are split in the course of the synthesis. In Walton, Wagner, Peterson, Holly and Folkers (J. Amer. Chem. Soc. 76 (1954), page 4748 et seq.) the intermediate product 7-carbethoxy-3-acetylthioheptanoic acid is split with L-ephedrine. Another process published by the same authors in J. Amer. Chem. Soc. 77 (1955) page 5144 involves the same intermediate product. Japanese patent 7970 describes the addition compound of alpha-lipoic acid with beta-cyclodextrin without mentioning the separation into enantiomeric compounds.

SUMMARY OF THE INVENTION

The object of the present invention is the preparation of enantiomerically pure salts of alpha-lipoic acid using an optically active auxiliary base and the subsequent liberation of the pure optical isomers of alpha-lipoic acid. In the pure optical isomers of alpha-lipoic acid (R- and S-form, i.e. R-alpha-lipoic acid and S-alpha-lipoic acid) the R-enantiomer is predominantly anti-inflammatory and the S-enantiomer is predominantly antinociceptive in contrast to the racemate (see EP 0,427,247, Nov. 8, 1990).

The present invention also provides a method for the preparation of salts of the pure optical isomers of alpha-lipoic acid with the pure optical isomers of alpha-methylbenzylamine. The method of the invention is carried out by dissolving the isomers in an appropriate solvent at elevated temperature, for example at 30°-60° C., in particular at 40° C., and isolating the pure diastereomeric salts by crystallization at low temperature, for example at 10° C. to 30° C., in particular at 25° C. Solvents apart from water that may be used for this purpose are: aliphatic hydrocarbons with a carbon chain length between 3 and 10 carbon atoms, aromatic hydrocarbons that are liquid, esters of aliphatic or cycloaliphatic carboxylic acids with 2 to 6 carbon atoms and aliphatic or cycloaliphatic alcohols with 2 to 6 carbon atoms, aliphatic or cycloaliphatic alcohols with 1 to 6 carbon atoms, ethers and glycol ethers or homogeneous mixtures of the solvents named. Particularly preferred solvents are toluene, acetic acid ethyl ester and cyclohexane. To prepare the diastereomeric salts the mixture of free R-alpha-lipoic acid and S-alpha-lipoic acid is then preferably either directly reacted with alpha-methylbenzylamine or also the mixture of R-alpha-lipoic acid and S-alpha-lipoic acid as a salt, e.g. alkali or ammonium salt is reacted with a salt of alpha-methylbenzylamine, e.g. hydrochloride or acetate. It is also possible to react an alkaline earth salt of alpha-lipoic acid with a sulfate of alpha-methylbenzylamine.

It has surprisingly been found that the diastereomeric salt pairs display differences in solubility with the result that, when reacting the racemate of alpha-lipoic acid with an optically pure isomer of alpha-methylbenzylamine, one diastereomeric salt pair is selectively isolated. It is particularly advantageous to add to the racemic alpha-lipoic acid solution only 0.3–0.8, but preferably 0.5–0.6 of the molar equivalent of a pure enantiomer of alpha-methylbenzylamine. When this is done, it is possible to selectively prefer a diastereomeric salt pair. The enantiomer of alpha-lipoic acid, now greatly enriched in the mother liquor, can be obtained in particularly enriched form through addition of the other enantiomer of alpha-methylbenzylamine. This procedure is suitable for a continuous preparation process of both R-alpha-lipoic acid and S-alpha-lipoic acid, it being possible to obtain the two pure enantiomers substantially quantitatively. These diastereomeric salt pairs can be purified through recrystallization from the pure, above mentioned solvents or homogeneous mixtures of them, so that pure salt pairs are finally obtained.

The pure salt pairs of R-alpha-lipoic acid and R-alpha-methylbenzylamine or S-alpha-lipoic acid and S-alpha-methylbenzylamine may be split by addition of acids, e.g. mineral acids, and the pure R-alpha-lipoic acid or the pure S-alpha-lipoic acid isolated by extraction. The purity of the optical isomers and the diastereomeric salt pairs was determined using the specific optical rotation values.

Relative contents of the optical isomers of alpha-lipoic acid were then determined by gas chromatography in optically active columns with a detection limit >0.5%. The values are given as enantiomer excesses (ee-values).

Enantiomerically pure R-alpha-lipoic acid or S-alpha-lipoic acid can be converted with diphenylmethylamine into a stable salt that is easy to handle; the optical purity of alpha-lipoic acid can then be determined via the specific optical rotation value.

DETAILED DESCRIPTION OF PREFERRED EMBODIMENTS

The following examples illustrate preferred embodiments of the invention:

Example 1

20.6 g (100 mmol) R-alpha-lipoic acid were dissolved at 40° C. in 200 ml toluene. 12.1 g (100 mmol) R-(+)-alpha-methylbenzylamine were added within 5 minutes. The mixture was cooled to 25° C. over 2 hours. The precipitate was filtered off and rewashed twice with, in each case, 30 ml toluene. The salt pair was dried in a vacuum at 45° C. 32.4 g (99% of theory) were obtained.

R-alpha-lipoic acid-R-alpha-methylbenzylamine salt, alpha$_D^{20}$= +74.0°
(c=1; ethanol), ee.: >99% (GC) solubility in toluene 0.09% (25° C.), in water 1.16% (25° C.) melting point 109°–115° C.

Example 2

20.6 g (100 mmol) S-alpha-lipoic acid were dissolved at 40° C. in 200 ml toluene. 12.1 g (100 mmol) R-alpha-methylbenzylamine were added within 5 minutes. The mixture was cooled to 25° C. over 2 hours. The precipitate was filtered off and rewashed twice with, in each case, 30 ml toluene. The salt pair was dried in a vacuum at 45° C.
32.1 g (98% of theory) were obtained.
S-alpha-lipoic acid-R-alpha-methylbenzylamine salt, alpha$_D^{20}$= −59.2°
(c=1; ethanol), ee.: >99% (GC).
Solubility in toluene 0.12% (25° C.), in water 1.41% (25° C.) melting point: 113°–117° C.

Example 3

20.6 g (100 mmol) S-alpha-lipoic acid were dissolved at 40° C. in 200 ml toluene. 12.1 g (100 mmol) S-alpha-methylbenzylamine were added within 5 minutes and working carried out as described in Example 1.
32.3 g (99% of theory) were obtained.
S-alpha-lipoic acid-S-alpha-methylbenzylamine salt, −74.2°
(c=1; ethanol), ee.: >99% (GC).
Solubility in toluene 0.09% (25° C.), in water 1.17% (25° C.) melting point 109°–115° C.

Example 4

20.6 g (100 mmol) R-alpha-lipoic acid were dissolved at 40° C. in 200 ml toluene. 12.1 g (100 mmol) S-alpha-methylbenzylamine were added within 5 minutes and the process was carried out as described in Example 2.
32.0 g (98% of theory) were obtained.
R-alpha-lipoic acid-S-alpha-methylbenzylamine salt, alpha$_D^{20}$= +59.4°
(c=1; ethanol), ee.: >99% (GC).
Solubility in toluene 0.12% (25° C.), in water 1.40% (25° C.) melting point 113°–117° C.

Example 5

4.0 g (19.4 mmol) R-alpha-lipoic acid were dissolved at 40° C. in 30 ml diethyl ether and reacted with a solution of 3.55 g (19.4 mmol) diphenylmethylamine in 100 ml ether. The precipitate was crystallized out from 30 ml methanol/150 ml diisopropyl ether. 17.5 g (18.4 mmol) (95% of theory) were obtained.
R-alpha-lipoic acid-diphenylmethylamine salt with a melting point of 123°–4° C. ee.: >99%,
alpha$_D^{25}$= +58.8° (c=1.4; pyridine);
alpha$_D^{25}$= +60.2° (c=0.3; pyridine).

Example 6

With exclusion of light, a hot solution of 1.03 g (5 mmol) racemic alpha-lipoic acid in 75 ml of ethyl acetate dried with K$_2$CO$_3$ was reacted with 0.303 g (2.5 mmol) R-alpha-phenylethylamine and then cooled, first to room temperature and then in a refrigerator. 730 mg (89%) crystallized out which consisted mainly of the R-alpha-lipoic acid-R-alpha-methylbenzylamine salt. This was recrystallized twice from, in each case, 30 ml ethyl acetate, 550 mg (67%) purified diastereomeric salt being obtained.

To release the R-alpha-lipoic acid the salt was dissolved in water, the solution covered with a layer of ether and acidulated with shaking with 0.1 N hydrochloric acid. The R-alpha-lipoic acid was extracted three times with fresh ether, the combined ether phases were washed neutral and, after drying and evaporation, R-alpha-lipoic acid was obtained in virtually quantitative yield.

135 mg (0.654 mmol) of the R-alpha-lipoic acid so obtained were dissolved in 1 ml ether and reacted with the solution of 152 mg (0.83 mmol) diphenylmethylamine in 3.5 ml ether. The precipitate was recrystallized from methanol (1 ml) diisopropyl ether (5 ml). R-alpha-lipoic acid-diphenylmethylamine salt was obtained with a melting point of 120° C., alpha$_D^{20}$= +51° (c=0.3; pyridine).

Example 7

20.6 g (100 mmol) racemic alpha-lipoic acid were dissolved at 40° C. in 200 ml ethyl acetate. Over 5 minutes 6.59 g (54 mmol) R-(+)-alpha-methylbenzylamine were added thereto. The mixture was then cooled within 2 hours to 25° C. The precipitate was filtered off and rewashed twice with, in each case, 35 ml ethyl acetate. The moist salt pair was recrystallized four times from, in each case, 400 ml ethyl acetate and then dried in a vacuum at 45° C. 9.3 g diastereomeric salt were obtained from R-alpha-lipoic acid and R-(+)-alpha-methylbenzylamine, alpha$_D^{20}$= +66.0° (c=1; ethanol).

The salt pair was suspended in 300 ml water at 25° C. and reacted with 100 ml cyclohexane. The mixture was slowly adjusted to a pH value of 1 with 1 N hydrochloric acid with ice cooling and then heated to 40° C. The phases were separated and the water phase re-extracted once more with 30 ml cyclohexane. The combined cyclohexane extracts were cooled to 5–10° C. and post-stirred at this temperature for 5 hours for crystallization. The precipitate was filtered off, rewashed once with 30 ml cyclohexane and dried at 25° C. in a vacuum. 4.1 g (40% of theory) R-alpha-lipoic acid, alpha$_D^{28}$= +104.1° (c=1; benzene) were obtained.

Example 8

20.6 g (100 mmol) racemic alpha-lipoic acid were dissolved at 40° C. in 200 ml toluene. 6.59 g (54 mmol) R-(+)-alpha-methylbenzylamine were added over 5 min. The mixture was then cooled within 2 hours to 25° C., filtered and the sediment rewashed twice with in each case 35 ml toluene. The moist salt pair was recrystallized four times from, in each case, 400 ml toluene and then dried in a vacuum at 45° C. 10.6 g diastereomeric salt were obtained, alpha$_D^{20}$= +72.5° (c=1; ethanol).

The salt pair was split as described in Example 7 and the alpha-lipoic acid obtained in crystalline form from cyclohexane. 4.6 g (45% of theory) R-alpha-lipoic acid were obtained, alpha$_D^{28}$= +115.0° (c=1; benzene) ee.: >99% (GC).

Example 9

A) 103 g (500 mmol) racemic alpha-lipoic acid were dissolved at 40° C. in 1.0 l toluene. 33.0 g (270 mmol) R-(+)-alpha-methylbenzylamine were added within 5 minutes. The mixture was then cooled within 2 hours to 25° C., filtered and the precipitate washed twice with, in each case, 150 ml toluene.

The moist salt pair was recrystallized as described in Example 8. 53.0 g (162 mmol) R-alpha-lipoic acid- R-(+)-alpha-methylbenzylamine salt were obtained after drying.

The mother liquors of the recrystallization were substantially concentrated in a vacuum and the residue taken up with the crystallization mother liquor. This was extracted with 120 ml aqueous hydrochloric acid (solution R), sufficient hydrochloric acid being added for the aqueous phase to have a pH value of 1. The toluene phase was then washed twice with 100 ml water.

B) A further 66.0 g (320 mmol) racemic alpha-lipoic acid were dissolved in the toluenic alpha-lipoic acid solution from A) and reacted at 40° C. with 52.1 g (430 mmol) S-(−)-alpha-methylbenzylamine and then cooled within 2 hours to 25° C. The precipitate was filtered off and rewashed twice with in each case 150 ml toluene. The moist salt pair was recrystallized as described in Example 8. After drying, 91.7 g (280 mmol S-alpha-lipoic acid-S-(−)-alpha-methylbenzylamine salt were obtained. The mother liquors of the recrystallization were largely concentrated in a vacuum and the residue taken up with the crystallization mother liquor. These were extracted with 170 ml aqueous hydrochloric acid (solution S), sufficient hydrochloric acid being added so that the aqueous phase had a pH value of 1. The toluene phase was then washed with twice 100 ml.

C) A further 51.6 g (250 mmol) racemic alpha-lipoic acid were dissolved in the toluene/alpha-lipoic acid solution from B) and reacted at 40° C. with 47.3 g (390 mol) R-(+)-alpha-methylbenzylamine and worked up as described above under A). 83.2 g (254 mmol) R-alpha-lipoic acid-R-(+)-alpha-methylbenzylamine salt were obtained.

D) A further 51.6 g (250 mmol) racemic alpha-lipoic acid were dissolved in the toluene/alpha-lipoic acid solution from C) and reacted at 40° C. with 47.3 g (390 mol) S-(+)-alpha-methylbenzylamine alpha-methylbenzylamine and worked up as described under B). 81.2 g (248 mmol) S-alpha-lipoic acid-S-(−)alpha-methylbenzylamine salt were obtained.

E) 136 g (416 mmol) R-alpha-lipoic acid-R-(+)-alpha-methylbenzylamine salt were split as described in Example 2, 60.9 g (295 mmol) R-alpha-lipoic acid being obtained in crystalline form from cyclohexane. alpha$^{20}$ = +119.9° (c=1; ethanol);
alpha$_D^{20}$ = +117.2° (c=1.8; benzene);
ee.: >99%, mp.: 49°-50° C.

The mother liquor can be used for further crystallization trials. The hydrochloride solution of the R-(+)-alpha-methylbenzylamine was combined with the solutions R from A) and C), adjusted to a pH value of 13 with sodium hydroxide solution and extracted with toluene. The toluene phase was concentrated and yielded the R-(+)-alpha-methylbenzylamine in almost quantitative amount.

F) 172 g (528 mmol) S-(−)-alpha-lipoic acid-S-alpha-methylbenzylamine salt were split as described in Example 2, 75.3 g (365 mmol) S-alpha-lipoic acid being obtained in crystalline form from cyclohexane.
alpha$_D^{20}$ = −119.4° (c=1; ethanol); mp.: 49°-50° C.

The hydrochloride solution of S-(−)-alpha-methylbenzylamine was combined with solutions S from B) and D), adjusted to a pH value of 13 with sodium hydroxide solution and extracted with toluene. The toluene phase was concentrated and yielded S-(−)-alpha-methylbenzylamine in almost quantitative amount.

Example 10

14.0 g sodium hydroxide were prepared in 130 ml water. 20.6 g R-alpha-lipoic acid (100 mmol) were added at room temperature and post-stirred until a clear solution was obtained. 2.4 g (63 mmol) sodium borohydride dissolved in 35 ml water were then added dropwise at 20°-25° C. within 10 minutes. The mixture was then heated to 95° C. within 1 hour and post-stirred at 95° C. for 4 hours. After cooling, 100 ml toluene were added and adjusted to a pH value of 1-1.5 at 10°-15° C. with semi-concentrated hydrochloric acid. After phase separation the water phase was extracted once again with 50 ml toluene. The combined organic extracts were concentrated in a vacuum. 20.3 g (98% of theory) of R-6,8-dimercaptooctanoic acid were obtained. The distillation supplied 18.5 g. (bp 145°-6° C., 0.3 mbar). alpha$_D^{20}$: −10.7° (C=1, ethanol).

Example 11

21.0 g sodium hydroxide were prepared in 195 ml water. 30.9 g S-alpha-lipoic acid were added at room temperature an stirred until a clear solution was obtained. 3.6 g (95 mmol) sodium borohydride dissolved in 50 ml water were then added dropwise within 10 minutes. The mixture was then heated to 95° C. within 1 hour and post-stirred at 95° C. for 4 hours. After cooling, 150 ml toluene were added and adjusted to a pH value of 1-1.5 at 10°-15° C. with semiconcentrated hydrochloric acid. After phase separation the water phase was extracted once again with 75 ml toluene.

The combined organic extracts were concentrated in a vacuum. 30.3 g (97% of theory) of R-6,8-dimercaptooctanoic acid were obtained. The distillation supplied 28.7 g. (bp 145°-6° C., 0.3 mbar).
alpha$_D^{20}$: +10.7° (C=1, ethanol).

What is claimed is:

1. A salt pair selected from the group consisting of (a) a salt pair composed of R-alpha-lipoic acid and R-(+)-alpha-methylbenzylamine, (b) a salt pair composed of R-alpha-lipoic acid and S-(−)-alpha-methylbenzylamine, (c) a salt pair composed of S-alpha-lipoic acid and R-alpha-methylbenzylamine and (d) a salt pair composed of S-alpha-lipoic acid and S-(−)-alpha-methylbenzylamine.

2. A salt pair composed of R-alpha-lipoic acid and R-(+)-alpha-methylbenzylamine.

3. A salt pair composed of R-alpha-lipoic acid and S-(−)-alpha-methylbenzylamine.

4. A salt pair composed of S-alpha-lipoic acid and R-alpha-methylbenzylamine.

5. A salt pair composed of S-alpha-lipoic acid and S-(−)-alpha-methylbenzylamine.

6. A method for the preparation and isolation of salts of the pure optical isomers of alpha-lipoic acid and the optical antipodes of alpha-methylbenzylamine, said method comprising reacting a racemic mixture of R-alpha-lipoic acid and S-alpha-lipoic acid or any mixture of R-alpha-lipoic acid and S-alpha-lipoic acid with the optical antipodes of alpha-methylbenzylamine in solution, and allowing the diastereomeric compounds to crystallize out.

7. A method as set forth in claim 6 in which the reaction is carried out at a temperature between 20° C. and 60° C. and in which a precipitate of diastereomeric compound is obtained by cooling to 10° C. to 15° C.

8. A process as set forth in claim 6 or claim 7 including the additional step of filtering off the precipitated salt after the reaction and further processing the mother liquors.

9. A process for the isolation of the optically pure isomers of alpha-lipoic acid by splitting the pure diastereomeric salts of (R)-alpha-lipoic acid and alpha-methylbenzylamine and/or of S-alpha-lipoic acid and alpha-methylbenzylamine, said method comprising splitting the said diasteriomeric salt by reaction with inorganic or organic acids.

10. A method for the preparation of an optically pure enantiomer of 6,8-dimercaptooctanoic acid which comprises reducing an optically pure isomer of alpha-lipoic acid with sodium borohydride as a reducing agent.

* * * * *